US011486840B2

(12) United States Patent
Laakkonen et al.

(10) Patent No.: US 11,486,840 B2
(45) Date of Patent: Nov. 1, 2022

(54) ELECTRICAL TOMOGRAPHY FOR VERTICAL PROFILING

(71) Applicant: ROCSOLE LTD, Kuopio (FI)

(72) Inventors: Pasi Laakkonen, Kuopio (FI); Anssi Lehikoinen, Kuopio (FI); Mika Mononen, Kuopio (FI); Arto Voutilainen, Kuopio (FI)

(73) Assignee: Rocsole Ltd., Kuopio (FI)

( * ) Notice: Subject to any disclaimer, the term of this patent is extended or adjusted under 35 U.S.C. 154(b) by 193 days.

(21) Appl. No.: 16/645,270

(22) PCT Filed: Sep. 6, 2017

(86) PCT No.: PCT/FI2017/050628
§ 371 (c)(1),
(2) Date: Mar. 6, 2020

(87) PCT Pub. No.: WO2019/048727
PCT Pub. Date: Mar. 14, 2019

(65) Prior Publication Data
US 2020/0300795 A1 Sep. 24, 2020

(51) Int. Cl.
*G01N 27/02* (2006.01)
*G01N 33/28* (2006.01)

(52) U.S. Cl.
CPC ......... *G01N 27/02* (2013.01); *G01N 33/2847* (2013.01)

(58) Field of Classification Search
CPC .. G01N 27/02; G01N 33/2847; G01N 27/226; G01N 27/07
See application file for complete search history.

(56) References Cited

U.S. PATENT DOCUMENTS

| 3,933,030 A | 1/1976 | Forster et al. |
| 2002/0093348 A1 | 7/2002 | Buhler et al. |

(Continued)

FOREIGN PATENT DOCUMENTS

| ES | 2211336 A1 | 7/2004 |
| JP | H10122544 A | 5/1998 |

(Continued)

OTHER PUBLICATIONS

International Search Report and Written Opinion of the International Searching Authority issued in PCT/FI2017/050628, dated Feb. 7, 2018; ISA/FI.

*Primary Examiner* — Christopher P McAndrew
*Assistant Examiner* — Zannatul Ferdous
(74) *Attorney, Agent, or Firm* — Harness, Dickey & Pierce, P.L.C.

(57) ABSTRACT

An apparatus for determining, by electrical tomography, vertical profile of an electrical property of interest of material(s) in a target volume comprises a measurement probe to be positioned at a plurality of different measurement levels in a target volume and comprising a plurality of measurement elements each having an interface surface. Each interface surface has a size, shape, and rotational position. A measurement path is formed between two interface surfaces as dependent on the sizes, shapes, and rotational positions of the two interface surfaces, and the distance between the two interface surfaces. The locations, rotational positions, shapes, and sizes of the interface surfaces are selected to provide at least two different measurement paths differing from each other in one or more of said sizes of, shapes of, rotational positions of, and distances between the associated interface surfaces.

14 Claims, 5 Drawing Sheets

(56) References Cited

U.S. PATENT DOCUMENTS

| | | | |
|---|---|---|---|
| 2010/0018304 A1* | 1/2010 | McGregor | G01V 3/20 |
| | | | 73/152.18 |
| 2010/0299068 A1* | 11/2010 | Mason | G01N 27/07 |
| | | | 702/7 |
| 2011/0025336 A1* | 2/2011 | Forgang | G01V 3/20 |
| | | | 324/367 |
| 2011/0198078 A1* | 8/2011 | Harrigan | E21B 49/087 |
| | | | 166/254.2 |
| 2013/0038337 A1 | 2/2013 | Rodfalk et al. | |
| 2014/0013830 A1 | 1/2014 | Wang et al. | |
| 2014/0151273 A1 | 6/2014 | Lehikoinen et al. | |
| 2017/0067338 A1* | 3/2017 | Gisolf | E21B 49/10 |

FOREIGN PATENT DOCUMENTS

| JP | 2013195343 A | 9/2013 |
|---|---|---|
| WO | WO-0062100 A2 | 10/2000 |
| WO | WO-2017105432 A1 | 6/2017 |

\* cited by examiner

ELECTRICAL TOMOGRAPHY FOR VERTICAL PROFILING

CROSS-REFERENCE TO RELATED APPLICATIONS

This application is a 371 U.S. National Phase of International Application No. PCT/FI2017/050628, filed on Sep. 6, 2017. The entire disclosure of the above application is incorporated herein by reference.

TECHNICAL FIELD

The present specification relates generally to monitoring, utilizing electrical tomography, industrial processes where process fluids are stored in various types of containers. More specifically, the present specification is related to solutions for investigating vertical profiles of material conditions within such containers.

BACKGROUND

In various industries, there are processes where vertical profiles of various material conditions within process containers should be able to be investigated, for example, to monitor the status of various processes or the condition of the process equipment at issue.

For example, in the fields of oil production, transportation, and refining, oils of different degrees of refining may be collected into and stored in various types of tanks which may be several, and even tens of, meters high. Then, various substances contained in the oil, such as water, may be stratified into different layers at different heights. In such situations, the vertical profile of the material conditions in the tank may be of interest, for example, to determine appropriate height from which to pump oil out of the tank.

In many types of processes, such as those of the oil industry, the conditions within the process equipment may be harsh, setting high requirements as well for the measurement equipment as for the measurement method.

For example, various types of contamination materials may be accumulated or deposited onto the equipment surfaces and the surface of a measurement probe. Such unwanted deposit may have a strong effect on the measurements, thereby possibly affecting the reliability of the material conditions profiling.

SUMMARY

This summary is provided to introduce a selection of concepts in a simplified form that are further described below in the Detailed Description. This Summary is not intended to definitely identify key features or essential features of the claimed subject matter, nor is it intended to be used to limit the scope of the claimed subject matter.

In one aspect, an apparatus is disclosed which may be used for determining, by electrical tomography, vertical profile of an electrical property of interest of one or more materials present in a target volume on the basis of measurements of a measurable electrical quantity dependent on said electrical property of interest.

The apparatus comprises a measurement probe arranged to be positioned at a plurality of different, vertically separate measurement levels in a target volume to carry out the measurements of the measurable electrical quantity at the different measurement levels.

The measurement probe comprises a plurality of measurement elements each having an interface surface arranged to be, with the measurement probe positioned within the target volume, in measurement connection with the material(s) present in the target volume.

Each interface surface has a size, a shape, and a rotational position. A measurement path for measurement of the measurable electrical quantity is formed, with the measurement probe in use, between two interface surfaces. The measurement path is dependent on the sizes, shapes, and rotational positions of the two interface surfaces, and the distance between the two interface surfaces along the surface of the measurement probe. The locations, rotational positions, shapes, and sizes of the interface surfaces of the plurality of measurement elements are selected to provide at least two different measurement paths which differ from each other in one or more of said sizes of, shapes of, rotational positions of, and distances between the associated interface surfaces.

In another aspect, an electrical tomography method is disclosed which may be used for determining vertical profile of an electrical property of interest of material(s) present in a target volume on the basis of measurements of a measurable electrical quantity dependent on said electrical property of interest, carried out at a plurality of different measurement levels in the target volume by an apparatus in accordance with the first aspect discussed above.

The method utilizes measurements carried out, at least for one measurement level, via at least two different measurement paths. The method comprises determining an effect of possible contaminant accumulated on the measurement probe and the measurement elements thereof on the measurements on the basis of the measurements of the measurable electrical quantity via the at least two different measurement paths.

The electrical property of interest may be selected so as to represent material conditions within the target volume. Thereby, the profile determined for the electrical property of interest may be further used as an indication of those material conditions, especially the vertical profile thereof.

Many of the attendant features will be more readily appreciated as the same becomes better understood by reference to the following detailed description considered in connection with the accompanying drawings.

BRIEF DESCRIPTION OF THE DRAWINGS

The present description will be better understood from the following detailed description read in light of the accompanying drawings, wherein.

The drawings of FIGS. 1 to 6 are not in scale.

DETAILED DESCRIPTION

The detailed description provided below in connection with the appended drawings is intended as a description of a number of embodiments and is not intended to represent the only forms in which the embodiments may be constructed, implemented, or utilized.

At least some of the embodiments and examples discussed below may enable, for example, reliable determination of vertical profile of material conditions within a target volume in a process environment, taking into account possible contamination on the measurement probe and the measurement elements thereof.

Figure 1:
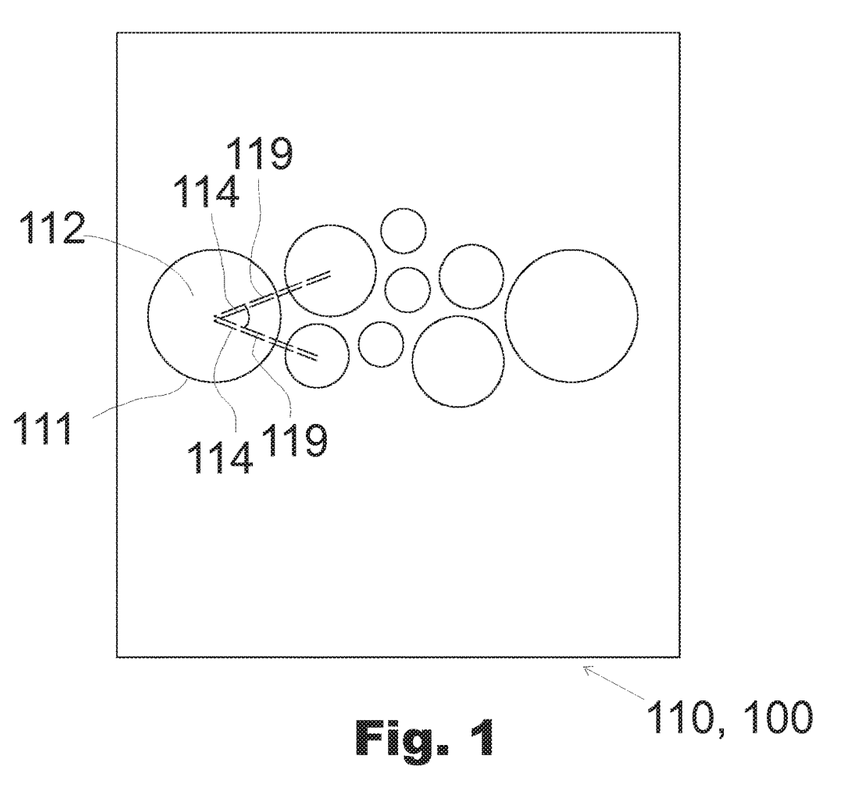
FIG. 1 illustrates schematically a front view of a measurement probe of an apparatus for electrical tomography.

The measurement probe 110 of FIG. 1 may be used as a part of an apparatus 100 for determining, by electrical tomography, a vertical profile of an electrical property of interest of material(s) present in a target volume. In FIG. 1, only the measurement probe 110 of the apparatus 100 is illustrated. In one embodiment, the measurement probe 110 alone forms the essence of such apparatus. In other embodiments, an apparatus may comprise, in addition to the measurement probe, also other elements such as controlling and/or computing system(s) configured to control the operation of the measurement probe and/or carrying out tomographic analysis on the basis of measurements carried out by the measurement probe. In both cases, the measurement probe thus serves as the actual measurement device, unit, or system of such apparatus, by which the actual measurements needed in the electrical tomography can be carried out.

"Electrical tomography" refers to electrical tomographic investigation methods, such as electrical tomographic imaging, covering various methods for investigating or monitoring a target region on the basis of determining an estimation of an electrical property of interest of one or more materials present in the target region. Generally, the target region may be a two-dimensional area or a three-dimensional volume. Said determination is carried out on the basis of basically non-invasive measurements of a measurable electrical quantity which may be the electrical property of interest itself, or a secondary, measurable electrical quantity dependent on, or proportional to, the actual property of interest.

The electrical property of interest may be, for example, electrical permittivity or conductivity. Then, the tomography process may fall within electrical capacitance tomography ECT or electrical impedance tomography EIT, respectively. In yet another possibility, the electrical property of interest may be electrical admittivity, combining those two above quantities. The admittivity is a complex valued quantity. However, the electrical property of interest is not limited to the examples above.

Basically, electrical tomography may be based, for example, on comparison of measured values of the measurable electrical quantity and corresponding simulations provided by an observation model for an approximation of the electrical property of interest conditions in the target region. An estimate of the property of interest may be determined in an iterative process comprising adjustment of the observation model on the basis of such comparison. Thereby, the property of interest conditions within the target region may be reconstructed.

Determining a "vertical profile" of an electrical property of interest refers to determining the electrical property of interest at different vertically separate levels, or heights. Then, actually the dependence of the electrical property of interest on height is determined. The vertical profile may be determined along a substantially vertically aligned profiling path, i.e. a profiling path oriented substantially along the direction of gravity. Alternatively, a profiling path may be oriented as deviating from such vertical direction, as far as there are vertically separate levels of heights along such non-vertical profiling path. "Vertical profile" may thus be considered as referring to the electrical property of interest as function of height. The electrical property of interest may be determined as a continuous function, or for discrete levels/heights which may coincide with the measurement levels discussed below.

The determination of the electrical property of interest may comprise determination of the spatial distribution of that property in the surroundings of the measurement probe. Then, the property of interest conditions determined by the electrical tomography process may be represented as images, e.g. as two-dimensional cross-sectional images of the target volume. In such approach, the method may be considered as electrical tomographic imaging. On the other hand, the method above is not necessarily pure "imaging" comprising such image reconstruction. Then, distribution of the electrical property of interest may be presented in any other appropriate manner. In some applications, it may be sufficient to determine, for a given level or height, just one or more characteristic parameter values indicating or representing an average value of the electrical property of interest conditions at that level or height.

The basic principles of electrical tomography are well known for those skilled in the art. In the case of electrical tomographic imaging, various image reconstruction algorithms known in the art may be used.

The estimated and thereby "determined" property of interest may further be used as an indication of various material conditions in the target volume. For example, abrupt changes in the property of interest may indicate boundaries between different materials or material phases. Such boundaries may provide information, for example, on segregation or mixing of such different materials or material phases.

The "target volume" refers to a volume of interest in a process container containing one or more materials, the internal material conditions of which volume of interest are to be determined. The "process" may refer to any kind of industrial process e.g. in oil production, refining, and transport, other oil based industries, energy production, pulp industry, and food industry, without limiting the scope of this specification to these examples only. The material(s) presented in such process container may be in liquid or gaseous form. There may be also some amount of solid constituents within a fluid.

The measurement probe 110 is arranged to be positioned at different, vertically separate measurement levels in the target volume so that measurements of the measurable electrical quantity may be carried out at the different measurement levels. One example of such arrangement is illustrated in FIG. 2.

Figure 2:
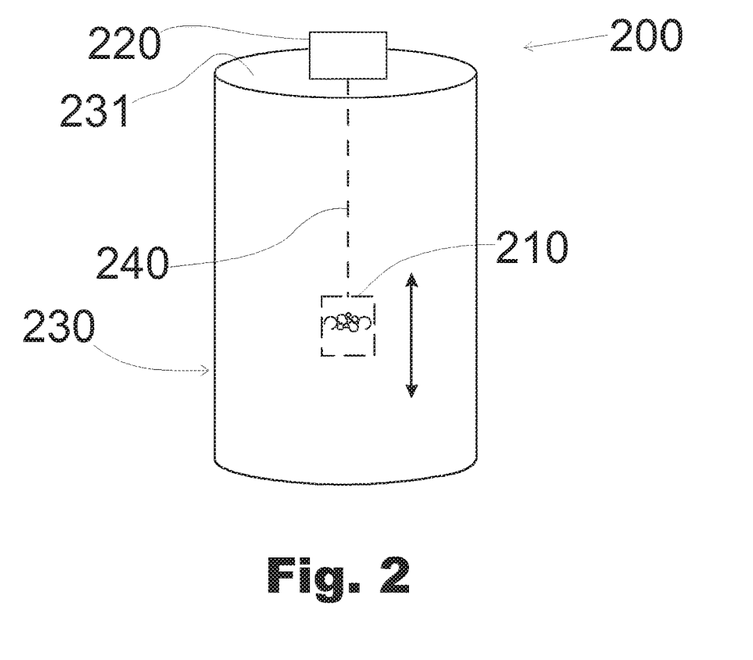
FIG. 2 illustrates schematically an apparatus comprising a measurement probe, installed in a container.

In the example embodiment illustrated in FIG. 2, an apparatus 200 comprises, in addition to a measurement probe 210 which may be in accordance with that of FIG. 1, an anchoring arrangement 220 which may be anchored in an upper wall or cover 231 of a tank 230, the upper wall or cover serving as a support structure of the tank. The measurement probe is connected to the anchoring arrangement, for example, via one or more cables or ropes 240, so that it is vertically movably suspended from the anchoring arrangement.

The anchoring arrangement may comprise, for example, any appropriate type of reel, rotation of which allows vertically moving the measurement probe at desired measurement levels. In one embodiment, the one or more cables or ropes may comprise an electrical cable via which power and/or control signals may be supplied to the measurement probe. Further, such cable(s) may be used for transmitting the measurement data from the measurement probe. In another embodiment, control signals and/or measurement data may be transmitted between the measurement probe and any appropriate control or computing unit by wireless transmission. For example, measurement data may be transmitted to an external data server or to a cloud service, from which it may be obtained for carrying out the actual data processing or computing phase of the tomography process. It is also possible that control and power equipment are included in or carried by the measurement probe itself.

Instead of, or in addition to, a suspending arrangement, an anchoring arrangement may comprise a guide rail along which the measurement probe is movable.

Various arrangements may be used for determining the height position of the measurement probe, i.e. the measurement level. In the case of a motorized reel of an anchoring arrangement, the position may be determined on the basis of the operation of such reel. In an embodiment where the measurement probe itself includes or carries suitable control equipment, the location may be determined by such control equipment on the basis of a starting position and moving speed of the measurement probe. In yet another approach, an external position detection arrangement of any appropriate type may be utilized.

Referring back to FIG. 1, the measurement probe 110 comprises a plurality of measurement elements 111, each of which has an interface surface 112. "Interface surface" refers to an surface forming an interface between the measurement element and the ambient, via which interface electrical measurement signals may be transmitted between the measurement element and the ambient. Said electrical signals may be, for example, voltage or current signals measured between two interface surfaces.

Each interface surface is so arranged in the measurement probe that when the measurement probe is positioned within a target volume to be investigated, the interface surface is in measurement connection with the material(s) present in the target volume.

The measurement connection between the measurement elements and the material(s) present in the target volume refers to the measurement elements' capability to supply and receive electrical measurement signals to and from the target volume with one or more materials present therein so that observations, i.e. measured values, of the measurable electrical quantity may be formed on the basis of those signals.

The measurement elements may comprise, for example, conductive electrodes forming the interface surfaces capable of supplying and receiving voltage and/or current signals to and from the target volume, respectively. The interface surfaces may be arranged to be in direct contact with the target volume and the material(s) therein.

Figure 3:
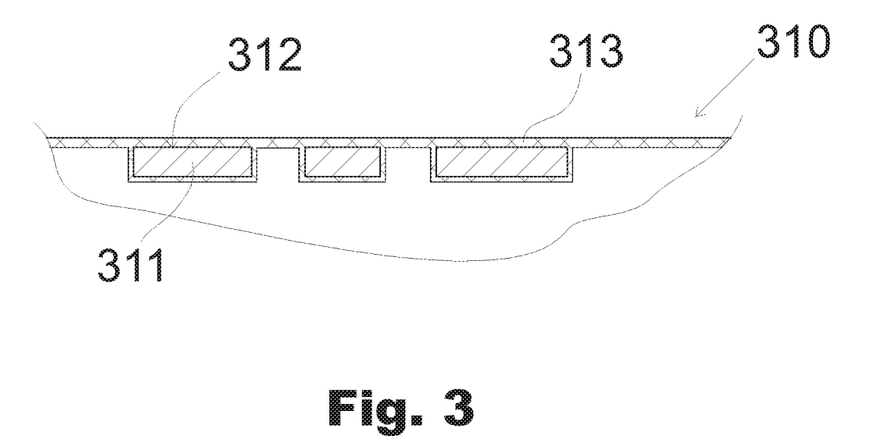
FIGS. 3 and 4 illustrate schematically partial sectional views of measurement probes for electrical tomography.

In an alternative embodiment illustrated in FIG. 3, the measurement probe 310 comprises an electrically insulating layer 313 covering the interface surfaces 312 of the measurement elements 311.

"Electrically insulating layer" refers to a layer formed of material(s) resulting in the electrical conductivity of that layer lying below $10^{-5}$ S/cm, preferably below $10^{-13}$ S/cm. An electrically insulating layer may enable adjusting, by proper selection of the insulating layer material and thickness, the dynamical range of the measurements appropriately in accordance with the impedance of the material(s) present in the target volume. An insulating layer may comprise, for example, polytetrafluoroethylene (PTFE). Thickness of an electrically insulating layer may lie, for example, in the range of 10 μm to 1 mm.

The measurement probe 310 of FIG. 3 has a plurality of measurement elements 311, three of which are visible in the partial illustration of FIG. 3.

In the example embodiment of FIG. 3, the measurement elements 311 are embedded in recesses formed in the body of the measurement probe so that the interface surfaces 312 lie at the level of the outer surface of the body of the measurement probe 310. In other embodiments, different arrangements are possible where, for example, the measurement elements protrude outwards from the outer surface of a body of a measurement probe.

In the example embodiment of FIG. 3, there are small gaps in the recesses between the measurement elements 311 and the outer surface of the measurement body. In the case of an electrically conductive material of the body of the measurement probe, such gap may be used to electrically isolate the measurement elements from the measurement probe body, and the gap may be filled with an electrically insulating material. In the example embodiment of FIG. 3, the material forming the electrically insulating layer 313 fills also said gaps. In embodiments with an electrically insulating material of the body of the measurement probe, the measurement elements may be in direct contact with such body.

Referring back to FIG. 1, each interface area 112 has a specific size and shape. In the example embodiment of FIG. 1, the interface areas are round. In other embodiments, interface areas may have different shapes. The interface areas 112 of the measurement probe 100 of FIG. 1 have different sizes. In other embodiments, all interface areas may have the same size. They may be located in any appropriate regular or irregular pattern.

In various embodiments, each interface area also has a rotational position. The rotational position is defined by the direction of rotation of the shape of the interface surface around a fictitious axis directed parallel to the normal of the interface surface. In other words, "rotational" and "rotation" refers to rotation in the plane of the interface surface. Such fictitious axis may be considered as extending, for example, through a geometric center point of the interface surface. In the case of a round or circular shape, the rotational direction of the shape actually has no effect on the operation of the associated electrode, assuming the properties of the interface surface are constant over the whole area thereof.

The interface areas configured to be in measurement connection with the material(s) present in the target volume result, when the measurement probe is in use, in that a measurement path is formed between interface surfaces 112 of two measurement elements. Such measurement path refers to a path via which an electrical signal, such as a voltage or current signal, may be supplied and/or measured using the two measurement elements 111 at issue. The length and route of the measurement path is dependent on the distance between the two interface surfaces along the surface of the measurement probe. Said distance may be defined, for example, as the distance between the geometric center points of the interface surfaces. Further, the sizes and the shapes of the interface surfaces of the interface areas associated to a measurement path affect an effective width and cross-sectional shape of that measurement path. "Effective" width and shape refer to the volume surrounding a central line, within which volume major part of the electrical signal is concentrated.

Basically, the effective width and cross-sectional shape of a measurement path is also dependent on, thus affected by, the rotational positions of the associated two interface areas. However, in the case of round or circular or some other at least partially rotationally symmetric shapes, different rotational positions may result in identical measurement paths. That is the case, for example, with a square interface area, wherein a change of 90 degrees in the rotational position has no effect in the formed measurement path.

The distance between two interface surfaces along the surface of the measurement probe may be defined by a fictitious connecting line connecting the two interface surfaces. Then, said distance is defined by the length of the connecting line. In the case of a planar surface of the measurement probe, such connecting line is the shortest straight line between the geometric center points of the two interface surfaces. In the case of measurement probe with a curved surface, such connecting line following the shortest path between the geometric center points of the two interface surfaces is curved as defined by that curved surface.

Figure 4:
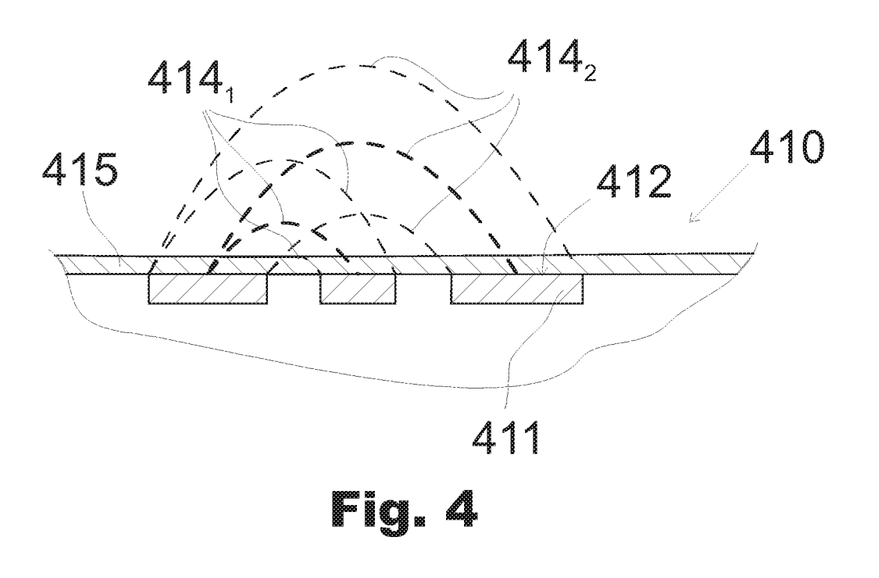

Whereas a connecting line follows the surface of the measurement probe, the corresponding measurement path typically extends above that surface. Said extension of example measurement paths above the measurement probe surface is illustrated in FIG. 4.

In FIG. 1, two connecting lines 119, associated to two measurement paths, are marked in the drawing of FIG. 1 by dashed lines. Projections of center lines of corresponding measurement paths 114 on the measurement probe surface are also marked schematically in the drawing of FIG. 1 as dashed lines. Similarly to the connecting lines 119, those projections are marked in the drawing as extending substantially between the centers, i.e. the geometric center points, of the associated interface surfaces. This is for simplicity of the illustration only. In practice, measurement paths in which the electrical signals are concentrated may extend differently, so that their center lines do not coincide with the centers of the interface areas.

In various embodiments, the locations, rotational positions, shapes, and sizes of the interface surfaces are selected so that a plurality of different measurement paths exists. Different measurement paths are such that they differ from each other at least in one or more of the following: the sizes of the associated interface surfaces, the shapes of the associated interface surfaces, the rotational positions of the associated interface surfaces, and the distances between the associated interface surfaces. "Differing" in the rotational position refers to such difference in the rotational positions of interface surfaces which affects the formation of the measurement path between the interface surfaces. Thus, for example, in the case of a round or circular shape, two measurement paths cannot distinguish from each other by the rotational positions of the associated interface surfaces only.

In various embodiments, there may be at least two different measurement paths. In the example embodiment of FIG. 1, with the total number of nine measurement elements of the example embodiment of FIG. 1, altogether 36 different measurement paths are formed between different pairs of measurement elements.

The at least two different measurement paths formed between the interface surfaces allow carrying out, for at least one measurement level, measurements of the measurable electrical quantity via the at least two different measurement paths. This may advantageously enable determining, as part of tomographic determination of the electrical property of interest profile in the target volume, an effect of a contaminant possibly accumulated on the measurement probe on the measurements. This is discussed further with reference to FIG. 4.

The measurement probe 410 of FIG. 4 may be basically in accordance with that illustrated in FIG. 3. The measurement probe 410 has an electrically insulating body, and there is no gap between the measurement elements 411 and that body. A layer of contaminant 415 is accumulated on the interface surfaces 412 of the measurement elements 411.

Two measurement paths $414_1$, $414_2$ are formed between the two pairs of interface surfaces. The measurement paths are schematically marked in the drawing of FIG. 4 by dashed center lines between the centres of the interface surfaces, and by dashed borderlines indicating the effective width of the measurement paths around the center lines thereof. For simplicity, the center lines are marked in the drawing of FIG. 4 as coinciding with the centers of the interface surfaces, although this is not necessarily the case in practice.

As can be seen in the drawing of FIG. 4, the layer of contaminant 415 covers different portions of the two measurement paths $414_1$, $414_2$. Thereby, it has different effects on the measurements of the measurable electrical quantity carried out via those two different measurement paths $414_1$, $414_2$. This may be utilized in the tomography process to find out the effect of the contaminant on the measurements, i.e. measured observations of the measurable electrical quantity, with higher reliability than in the case of utilizing measurements of just one measurement path or measurements of a plurality of several similar measurement paths, i.e. measurement paths with similar length and width.

The effect of possible contaminant on the measurements may be found out even more accurately on the basis of measurements of the measurable electrical quantity carried out via more than two different measurement paths. That way, the accuracy and reliability of the determination of the electrical property of interest may be improved even further. The most appropriate number of different measurement paths may depend also on the properties of the observation model used.

Measurements of the measurable electrical quantity via two or more measurement paths thus make it possible to determine the effect which possible contaminant lying, for example, as a continuous layer on the measurement probe and the interface surfaces of the measurement elements thereof has on the measurements. Then, that effect can be taken into account in the determination of the electrical property of interest, which may result in improved reliability or accuracy of said determination. The way of determining said effect of possible contaminant on the measurements is discussed further below with reference to the method of FIG. 7.

In addition, several measurements at the same measurement level, using several measurement paths, may naturally improve the accuracy of the determination of the electrical property of interest outside the possible contaminant layer. This may be, first, due to the increased amount of measurement data available for comparing the measurements with simulated observations provided in accordance with the observation model. Second, also the use of different measurement paths as such may improve said accuracy, because the measurements are collected from different regions of the target volume.

It is to be noted that for a given measurement probe and measurement element arrangement thereof, the measurement paths and their effective widths and cross-sectional shapes are not constant in that they would depend on the structure and layout of the measurement probe and the measurement elements thereof only. Instead, they may vary depending on the material(s) present, and/or on the homogeneity of the material conditions, in the target volume.

Thus, for two particular interface surfaces of measurement elements of a measurement probe, the actual measurement path may vary depending on the conditions in and type of the target volume in which the measurement probe is positioned. Further, the measurement path may vary as dependent on the type of the electrical signals used in the measurements. In any case, a measurement path "depend on" the sizes of, the shapes of, and the rotational positions of the two interface surfaces, and the distance between the two interface surfaces along the surface of the measurement probe in that those factors affect the formation of the measurement path.

In the example embodiment of FIG. 1, the measurement elements are positioned so that several pairs of different measurement paths 114 exist in such a way that the two connecting lines 119 associated to a pair of different measurement paths extend at a non-zero angle relative to each other. Extending at "non-zero" angle relative to each other refers to the extension of the connecting lines of the two different measurement paths in such a way that they are not parallel. Thus, "non-zero" angle also covers angle of "not 180 degrees". This allows carrying out measurements of the measurable electrical quantity in different directions at each measurement level, which may further improve the accuracy of the determination of the electrical property of interest. Further, said extension at an angle enables positioning of the different measurement paths so that their lengths may be kept reasonable to prevent too high impedances over the measurement paths.

In alternative embodiments, the different measurement paths may extend in the same direction.

In the measurement probe 110 of FIG. 1, the interface surfaces 112 of the measurement elements 111 lie on a substantially planar surface. This approach is particularly useful in applications where, at each measurement level, it is sufficient to measure the measurable electrical quantity in/via a measurement region extending perpendicularly in front of a surface of the measurement probe, on which surface the measurement elements lie. That may be the case, for example, in applications where the material conditions in the target volume are uniform in the horizontal direction and vary in the vertical direction only.

Figure 5:
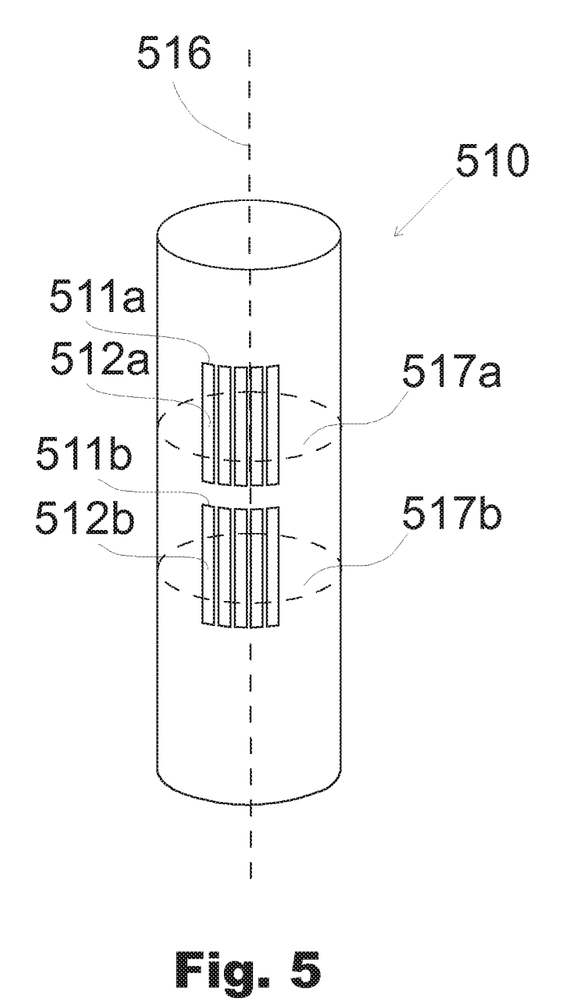
FIG. 5 illustrates schematically a perspective view of a measurement probe for electrical tomography.

The measurement probe 510 of FIG. 5 utilizes another approach in that the interface surfaces 512a, 512b of the measurement elements 511a, 511b lie on the cylindrical outer surface of the measurement probe. As being distributed on a curved, cylindrical surface, the measurement elements allow carrying out measurements of the measurable electrical quantity in a target region which extends as at least partially surrounding the measurement probe. In other embodiments, measurement elements or measurement element groups may be positioned at different sides along the circumference of a measurement probe, or distributed all over such circumference. In such embodiments, measurements of the measurable electrical quantity may be made all around the measurement probe.

The measurement probe 510 has a fictitious principal axis 516. The measurement probe is formed as an elongated body surrounding, and extending in the direction of, the principal axis, is arranged to be positioned at the different measurement levels with the principal axis oriented substantially vertically. This may be arranged, for example, by the measurement probe having a suspending arrangement configured to enable suspending the elongated measurement probe from an end thereof, whereby the measurement probe may be set vertically by the effect of gravity.

The measurement elements 511a, 511b of the measurement probe are distributed in two groups which are positioned at two different planes 517a, 517b which lie perpendicularly to the principal axis 516 of the measurement probe 510. This arrangement allows, first, carrying out measurements of the measurable electrical quantity at two different planes or sub-levels for each measurement level of the measurement probe, using one group of measure elements for one plane/sub-level. Further, this arrangement also increases the diversity of the measurements via enabling carrying out measurements via measurement paths formed by measurement elements of two different groups.

In other embodiments, there may be three or more groups of measurement elements distributed in three or more planes, respectively.

Each of the interface surfaces 512a, 512b of the measurement probe 510 of FIG. 5 has a length in a direction parallel to the principal axes 516, the length being substantially larger than the width of the interface surface. In the example embodiment of FIG. 5, the length is about ten times the width. In other embodiments, the length of an interface surface may be, for example, at least twice the width. With a length which is substantially higher than the width of an interface surface, it may be possible to have closely located interface surfaces with low impedances. Low impedance may be advantageous especially in the case of materials in the target volume having low electrical conductivity.

Apart from the curved surface of the measurement probe body, the arrangement between the measurement elements 511a, 511b and the body of the measurement probe 510 may be in accordance with any of the measurement probes discussed above with reference to FIGS. 3 and 4.

In any of the embodiments discussed above with reference to FIGS. 1 to 5, the sizes of the measurement probe and the measurement elements thereof may be selected, for example, in accordance with the properties of the process equipment in which the target volume lies, and intended resolution of the determination of the electrical property of interest. Minimum dimensions of the measurement elements may lie, for example, in the range of 2 to 3 mm. In some embodiments, also smaller minimum dimensions are possible, although the impedance increases when the size of a measurement element decreases. Maximum dimensions of the measurement elements may lie, for example, in the range of 1 to 5 cm. In some embodiments, such as in the case of narrow elongated shape of the measurement elements, the maximum dimensions may be even larger, for example, up to 10 cm.

The elongated interfaces surfaces 512a, 512b of the measurement probe 510 of FIG. 1 represent an example shape of an interface surface for which the rotational position of the interface surface may affect the measurement path. However in the example of FIG. 5, the rotational positions of all interface surfaces are the same, or they differ from each other by a degree of 180 degrees only, so that two measurement paths cannot differ by the rotational positions of the associated interface surfaces. In other embodiments, elongated interface surfaces may have several different rotational positions, wherein the rotational positions of the interface surfaces may be a property distinguishing two measurement paths from each other.

In the above, apparatuses are discussed with the main focus on measurement probe configurations and arrangements, as well as anchoring arrangements enabling anchoring the measurement probes, as being vertically movable, in or to a process equipment such as a container.

A measurement probe may be controlled by, and the measurements, i.e. the measurement data of the measured observations of the measurable electrical quantity, may be received by a computing system comprising any appropriate unit, sub-system, or arrangement configured to carry out the actual tomographic data analysis and determination of the electrical property of interest. Such computing system and the elements thereof may be configured to perform the operations of the tomography method in accordance with any of the embodiments discussed below with reference to the method aspect. A computing system may further comprise any appropriate unit, sub-system, or arrangement which is configured to control the operations of the measurement probe and/or the anchoring arrangement.

From another terminology point of view, a computing system or a part thereof "configured to" perform a specific method operation means actually that the computing system comprises "means for" performing that operation. The computing system may comprise separate means for different operations. Alternatively, any of such means for performing those various operations specified below may be combined so that more than one operation is carried out by the same means. It is even possible that all those operations are carried out by the same means, e.g. by single data processing apparatus.

Any means for performing any of such operations may comprise one or more computer or other computing and/or data processing components, units, devices, or apparatuses. In addition to actual computing and/or data processing means, the means for performing said operations may naturally also comprise any appropriate data or signal communication and connecting means, as well as memory or storage means for storing generated and/or received data.

Computing and/or data processing means serving as means for performing one or more of the operations of the electrical property of interest determination may comprise, for example, at least one memory and at least one processor coupled with the at least one memory. Then, the at least one memory may comprise computer-readable program code instructions which, when executed by the at least one processor, cause the apparatus to perform the operation(s) at issue. In addition to, or instead of, a combination of a processor, a memory, and program code instructions executable by the processor, means for performing one or more operations may comprise some hardware logic components, elements, or units, such as those examples mentioned below with reference to the method aspect.

A measurement probe and a computing system may be connected between any appropriate wired or wireless data connection enabling the control signal and measurement data transmission between the measurement probe and the computing system. Instead of directly transmitting the measurement data to the processing system, the measurement data may alternatively be transmitted from the measurement probe to an intermediate data storage, such as an external data server or a cloud service, for being transmitted therefrom to the computing system.

In one approach, an apparatus may thus comprise just a measurement probe, possibly accompanied by an anchoring arrangement. Then, measurement data produced by the measurement probe may be processed by any appropriate external computing system. In another approach, a complete tomographic apparatus may be implemented, comprising also any appropriate type of computing system. An example of the latter approach is illustrated in FIG. 6.

Figure 6:
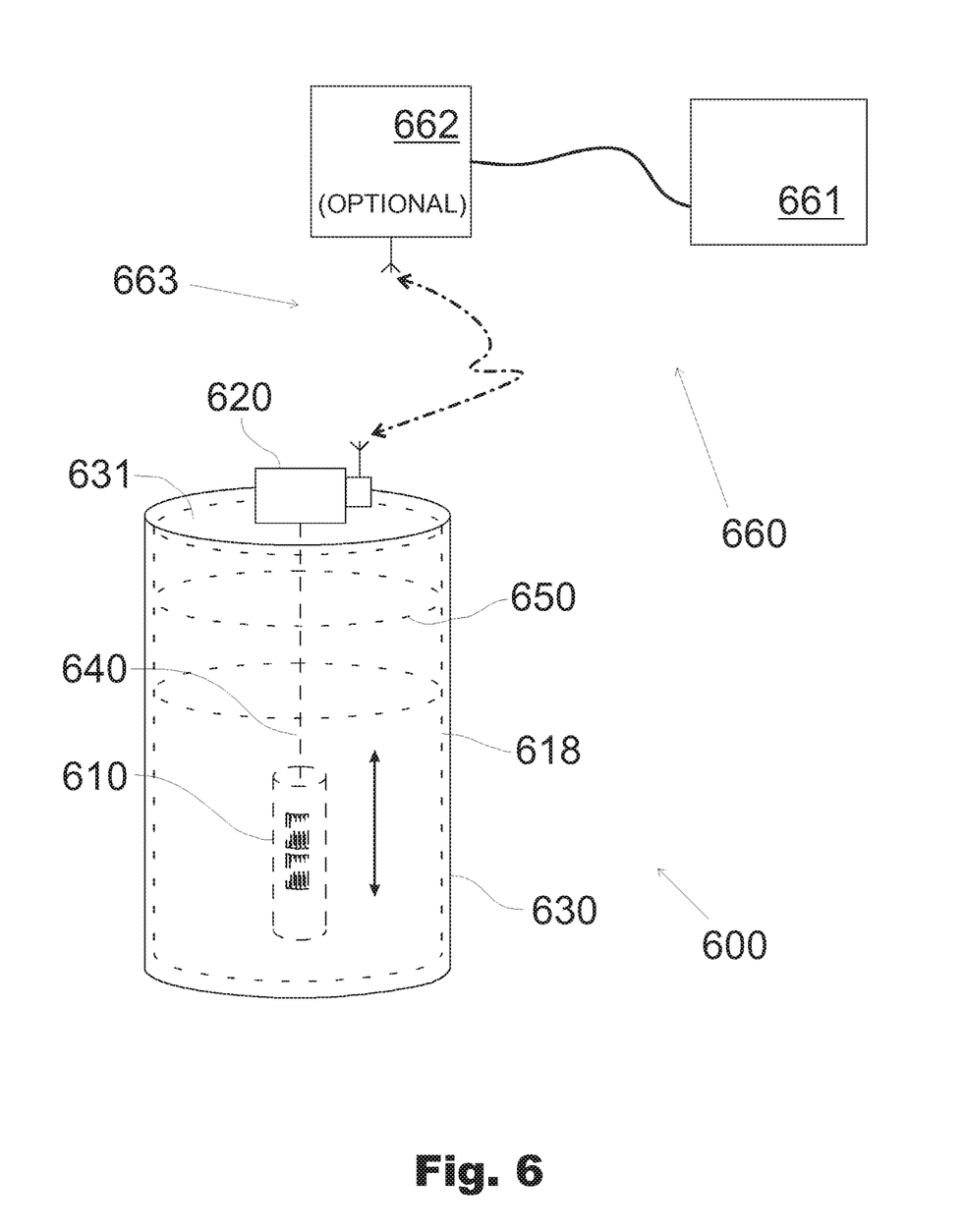
FIG. 6 illustrates schematically an apparatus for tomography, comprising a measurement probe, an anchoring system installed in a container, and a computing system.

FIG. 6 illustrates schematically an apparatus 600 by which an electrical tomography method for determining vertical profile of an electrical property of interest, such as permittivity, within a target volume 618 in a container 630 may be carried out. The container may be, for example, a tank for storing and/or processing oil therein. The target volume may comprise the entire width of the inner volume of the container, or it can comprise a narrower portion of the inner volume, surrounding a profiling path along which the measurement probe 610 is arranged to be movable.

The measurement probe 610 of the apparatus 600 may be in accordance with that discussed above with reference to FIG. 5. In other embodiments, measurement probes in accordance with any of those discussed above with reference to FIGS. 1 to 4 may be used.

In the example embodiment illustrated in FIG. 6, the measurement probe 610 is located within the process container 630 comprising a cover 631. An anchoring arrangement 620, which may be in accordance with any of those discussed above with reference to FIG. 2, is anchored or mounted to the cover 631.

The measurement probe is suspended from the anchoring arrangement 620 via one or more ropes or wires 640 such a way that it may be moved vertically at desired measurement levels 650 in the target volume 618. In other embodiments, in addition to or instead of a suspending arrangement, a measurement probe may be arranged to move along a guide rail.

The apparatus comprises further a computing system 660 connected to the measurement probe 610 to receive measured values of the measurable electrical quantity therefrom.

In the operational core of the computing system 660, there is a computer 661, comprising an appropriate number of memory circuits and processors for receiving, providing, and/or storing an observation model, measured data, estimate data, and for performing the computational operations of the tomography process.

The computing system further comprises a measurement electronics unit 662 configured to control the operation of the measurement probe 610 and receive the measurements therefrom. In the example embodiment illustrated in FIG. 6, the measurement electronics unit 662 and the measurement probe 610 are connected via a two-directional data connection arrangement 663, via which the measurement electronics unit may control the operation of the measurement probe and via which the measurement data collected by the measurement probe may be transferred to the measurement electronics unit and further to the computer 661.

In FIG. 6, the data connection arrangement 663 is illustrated as a wireless one. However, as is clear for a skilled person, this is one example only. In other embodiments, any appropriate type of connection, including wired ones, between the measurement electronics unit and the measurement probe, and generally between a measurement probe and a computing unit is possible which allows receiving measurement results from the measurement probe. The same connection may also allow controlling the measurement probe.

In the example embodiment illustrated in FIG. 6, the measurement electronics unit 662 is connected to the computer 661 so that the measurement electronics unit can be controlled by the computer, and that the measurement results can be sent to and received by the computer for further processing. The computer may comprise program code instructions, stored in a memory and configured to control, when run in a processor, the computer to carry out the operations of the method.

As a result of the method performed by the apparatus 600, vertical profile of the estimated electrical property of interest conditions in the target volume may be reconstructed. The electrical property of interest may be, for example, electrical admittivity, permittivity, or conductivity. Different sub-volumes of the target volume having different electrical property of interest conditions may be observable in the so determined profile, indicating different material conditions in the corresponding sub-volumes. Such different material conditions may comprise, for example, different water or other impurity content in oil.

It is to be noted that a measurement system comprising a specific measurement electronics unit is one embodiment only. In other embodiments, a measurement probe may be configured to be moved by the anchoring arrangement and carry out the measurements independently with or without continuous controlling by an external control means. Further, a measurement probe may be configured to transmit the measurement data via a wireless or wired data transfer connection to a computing system which may be a part of the complete apparatus or an external apparatus, device, or system. Alternatively, a measurement probe may be configured to store the measurement data for later transfer. In the case of wireless data transfer between the measurement probe and the computing system, measurement data may be transferred continuously, at specific intervals, or after completing a measurement process or a specific phase thereof. As an alternative to wireless or wired data transfer connection, measurement data may be stored on any appropriate removable storage means which may be removed from the measurement probe and installed in the computing system for receiving the measurement data therefrom.

Further, it is to be noted that the separate computer 661 and the measurement electronics unit 662 represent one way of implementation of the apparatus only. Naturally, an integrated apparatus may be implemented comprising any appropriate type of computing unit. In such case, the measurement system, except of the actual measurement probe, and the computing system may be thus at least partially combined. Embodiments are also possible where no specific external measurement electronics unit outside the measurement probe is included in the measurement system. Further, a completely integrated apparatus is possible comprising all parts of the computing system and the measurement system in a single apparatus.

The computing system 660 may be configured to carry out any of the methods discussed below with reference to FIG. 7. In other embodiments, similar methods may be carried out by a computing system not necessarily being part of a complete apparatus comprising also a measurement probe. In one approach, a separate, standalone computing system may be configured to receive measurements, carried out by a measurement probe in accordance with any of those discussed above, from any type of physical data storage, such as a data server or a cloud service.

Figure 7:
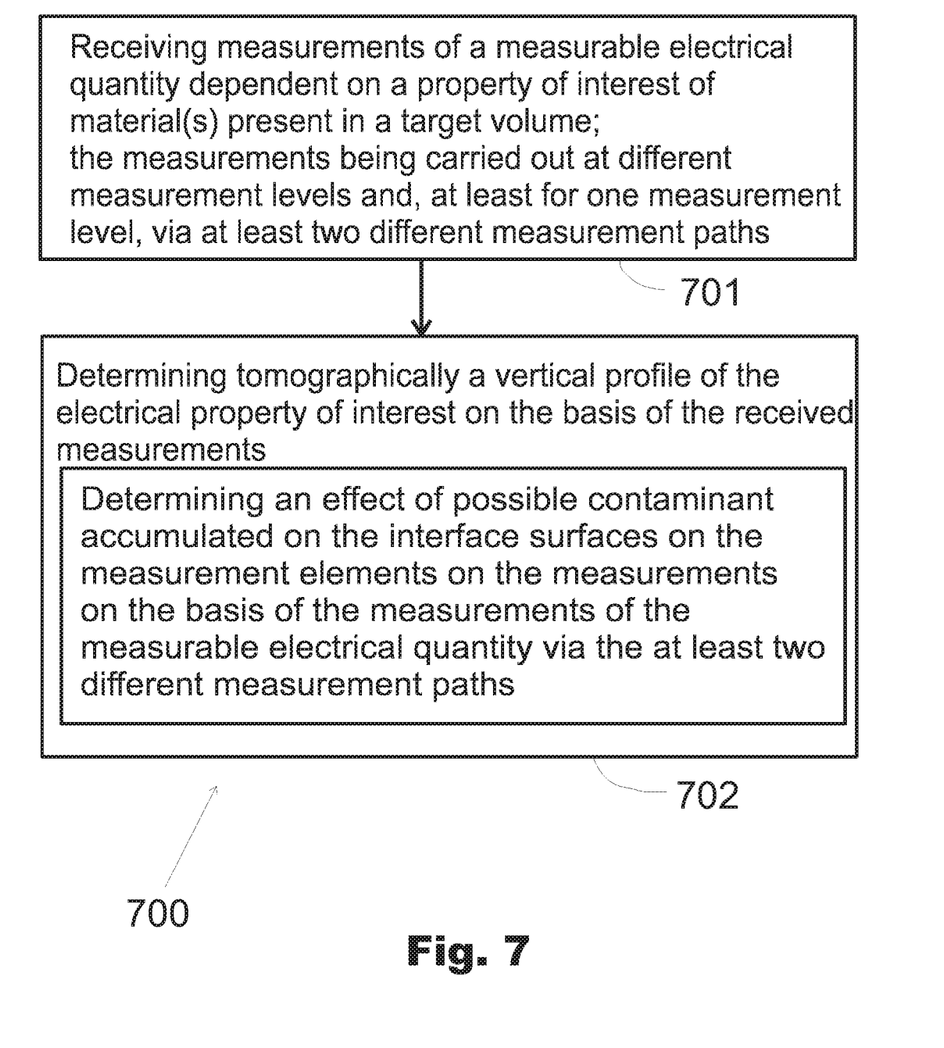
FIG. 7 illustrates a flow chart of a tomography method.

Irrespective of the means used for carrying out the method, the operations of the method 700 of FIG. 7 and the various embodiments thereof discussed above are preferably performed at least partially automatically by means of suitable computing and/or data processing means. Such means may comprise e.g. at least one processor and at least one memory coupled to the processor. The at least one memory may store program code instructions which, when run on the at least one processor, cause the processor to perform operations according to various operations of the method. Alternatively, or in addition, at least some of those operations may be carried out, at least partially, by means of some hardware logic elements or components, such as Application-specific Integrated Circuits (ASICs), Application-specific Standard Products (ASSPs), or System-on-a-chip systems (SOCs), without being limited to those examples.

The tomography method 700 of FIG. 7 is used for determining vertical profile of an electrical property of interest of material(s) present in a target volume in a container. In the method, said profile is determined on the basis of measurements of a measurable electrical quantity which is dependent on said electrical property of interest. The measurements are carried out at a plurality of different measurement levels by a measurement probe of an apparatus which may be in accordance with any of the apparatuses discussed above with reference to FIGS. 1 to 6.

The electrical property of interest may be, for example, electrical admittivity, permittivity, or conductivity.

The electrical property of interest may be dependent on, and it may thus indicate, any appropriate material condition (s) in the target volume. In an embodiment, the target volume comprises oil, and the electrical property of interest is dependent on water content of the oil. In this embodiment, the profile of the electrical property of interest determined in the method may be used for further determining or monitoring the vertical profile of water content of the oil as the material condition in the target volume.

As discussed above, "tomography" method may basically refer to a process where true, measured observations of a measurable electrical quantity are compared with corresponding simulated, approximate observations defined by an observation model. An observation model refers to a model which defines the relationship between simulated observations of the measurable electrical quantity, and the electrical property of interest of material(s) present in the target volume. The simulated observations corresponding to measurements, i.e. measured observations, made by a measurement probe. Basically, the observation model may be provided in accordance with the principles known in the field of electrical tomography. The observation model may define said relationship by means of any appropriate mathematical functions, elements, and operations.

As is clear for a person skilled in the art of electrical tomographic methods, "corresponding to measurements made by the measurement probe" means that the simulated values shall correspond to the measured ones in the sense that they are simulated for the same measurement setup with a specific measurement element arrangement and intended measurement geometry, and for the same measurement procedure with specific types of excitation and response signals, as which are intended to be used in the actual, real measurements.

Also other approaches are possible. For example, distribution of the electrical property of interest in the target volume may be determined using taught neural network(s). In such approach, the measurement data may be supplied to an appropriately taught neural network which then provides an estimate of the electrical property of interest conditions in the target volume, including possible contamination layer, without need for an observation model. Also in this kind of approach, an observation model may be used in teaching the neural network.

The method 700 of FIG. 7 comprises receiving, in operation 701, measurement data which represents measured values of a measurable electrical quantity which is dependent on the electrical property of interest of one or more materials present in the target volume. The measured values are or have been measured at a plurality of different measurement levels, i.e. at different heights in the target volume. Further, the received measurement data comprises, at least for one measurement level, measurements carried out via at least two different measurement paths.

"Receiving" the measurement data, i.e. measurement results, of the measurable electrical quantity may mean just receiving the results, in the form of electronic data, of ready performed measurements. In other words, the method itself does not necessarily comprise performing the actual measurements, but the measured values of the measurable electrical quantity may be generated separately and just received, as measurement data, as a part of the method. The measurements may be carried out by a measurement probe from which the results of the measurements are transferred to an apparatus carrying out the actual analysis. The measurement results or the measurement data may also be stored in any appropriate memory means contained in the measurement probe, and collected or transferred therefrom afterwards. Such approaches allow, for example, an embodiment where the results of the measurements performed at a measuring site are sent electronically to an analysis site where the actual analysis and quantity of interest determination is carried out.

Alternatively, the method may also comprise performing measurements of the measurable electrical quantity, thereby providing measured values thereof. So, the method may comprise also generating the measured values which are then received for the actual analysis operations of the method. Such measurements may be performed according to the principles known in the field of tomographic investigation methods, in particular tomographic imaging, such as electrical tomographic imaging. Examples of such methods include electrical impedance tomography and electrical capacitance tomography.

The measurements may be performed generally according to the principles as such well known in the field of various measurement technologies and tomographic investigation methods. For example, in the case of permittivity as the electrical property of interest, the measured results may comprise current signals resulting in response to various voltage excitation signals.

Being dependent on the electrical property of interest of the material(s) present in the target volume includes that the electrical property of interest itself may be the measurable electronic quantity. Alternatively, the measurable electrical quantity may be a secondary electrical quantity dependent on, or proportional to, the electrical property of interest of material(s) present in the target volume. Then, the electrical property of interest is measured indirectly, by measuring the measurable electrical quantity.

In operation 702, the method 700 of FIG. 7 comprises the actual tomography computational process where the vertical property of the electrical property of interest is determined on the basis of the received measurements. In this operation, principles, processes, and algorithms may be used which are, as such, known in the art of electrical tomography. Examples of various algorithms for computational processes of electrical tomography are described, for example, in WO 2014/118425 A1, WO 2014/135741 A9, and WO 2016/110608 A1.

As known for a skilled person, in tomographic investigating methods it is necessary to define a mapping that maps measurement data to the quantity of interest. In general, this mapping is called the inverse mapping in contrast to forward mapping the output of which is measurement data when the quantity of interest is used as an input. In the case of electrical tomographic measurements, the forward mapping is fundamentally the Maxwell's equations which, under certain conditions and assumptions, can be formulated in a simpler form known in the field of electrical tomography. In practical applications, the forward model can be understood as a numerical approximation of the governing partial differential equation (PDE) model.

There are different ways of constructing the inverse mapping in various tomographic and non-tomographic applications. The inverse mapping is often based on a more or less accurate numerical implementation of the governing PDE model. Depending on a case, the inverse mapping can also include other models for the quantity of interest, often referred to as prior models, as well as some parameterizations of the quantity of interest. Such models are usually independent on measurement data, and they used to incorporate some presumed properties and possible simplifications of the quantity of interest into the formulation of the inverse mapping. The inverse mapping must also define the nature of ultimate outcome of the mapping, which may depend on the perspective of the person constructing the model. In deterministic approaches, the outcome is usually defined as a value that gives a sufficiently close match between the measured and modeled data sets and is in accordance with the prior models. In other words, the outcome is a solution of an optimization problem the objective function of which consists of various terms with different weights. On the other hand, from the Bayesian viewpoint the goal is to formulate the solution as a probability density function, known as a posterior density, consisting of probability densities defined by the observation model, noise model and prior assumptions and models. Posterior densities may not be visually informative especially in high-dimensional cases. Therefore, the final outcome of the inverse mapping may be defined as some point estimate with appropriate confidence intervals. The computation of the point estimates and confidence intervals may necessitate various computational techniques. The above principles can be extended to situations of continuous measurements and online imaging. In such cases it may be beneficial to employ models for the temporal behavior of the quantity of interest, which leads to a recursive update process of prior models.

In the above, the inverse model very much relies on the physical observation model and its numerical approximation. However, it is evident that it is possible to construct inverse mapping also without any physical observation model, and some such approaches are briefly discussed in the following. In its simplest form, but not necessarily applicable in the field of electrical tomography, the inverse mapping may consist of a lookup table if the features of the quantity of interest are clearly visible in measurement data. More sophisticated computing approaches successfully used in many fields of applications to model complex relationships between inputs and outputs are artificial neural networks. Such approaches, not requiring explicit observation models when appropriate training sets are available, have been used also for image reconstruction in electrical tomography.

The determined electrical property of interest and the profile thereof may be considered as indicating various material conditions in the target volume, such as mixing of and interfaces between different materials or material phases. For example, abrupt changes in the profile of the electrical property of interest conditions close to the boundary surface may be interpreted as material or phase interfaces of different layers present in the target volume. On the other hand, a gradually changing property of interest along a profiling path may indicate a gradually changing material condition, such as water content in oil.

As is clear for a skilled person in the art, if the material conditions in the surroundings of the measurement elements are assumed to be homogeneous and no contamination layer is taken into account, the determined profile of the electrical quantity of interest may be erroneous. Presence of a contamination layer may strongly affect the measurements. Therefore, all models involved in the inverse mapping should account for possible existence of such contamination layer.

Thus, in the case of an observation model utilized in the process, in order to take into account possible contamination layer on the measurement probe, the observation model may be provided so as to define the simulated observations of the measurable electrical quantity to correspond to measurements made with the measurement probe in the reference position, and be dependent on both the electrical property of interest conditions farther away from the measurement probe, and the electrical property of interest of a contamination layer. This may be implemented, for example, by that the observation model allows the electrical property of interest conditions in a surface layer close to the surface of the measurement probe, the surface layer modelling the possible contamination layer, be clearly different from the electrical property of interest conditions elsewhere in the target volume.

Even if a contamination layer is included in the observation model, it may be possible that several combinations of a contamination layer material(s) and thickness provide the same result in single measurement carried out via one specific measurement path. In other words, good correspondence between simulated and measured values of the measurable electrical quantity may be achieved even though the actual contamination layer differs clearly from that approximated in the observation model. Therefore, the method 700 of FIG. 7 advantageously comprises determining an effect which possible contaminant accumulated on the measurement probe and the measurement elements thereof has on the measurements. Said effect is determined on the basis of the measurements of the measurable electrical quantity via the at least two different measurement paths.

Advantages achievable by said utilization of at least two different measurement paths were discussed above with reference to FIG. 4.

To summarize, basically, the principle of the method 700 of FIG. 7 is to provide an estimation of the profile of the electrical property of interest i) with good correspondence between the simulated and measured observations, i.e. simulated and measured values of the measurable electrical quantity; ii) which estimation possesses features in accordance with assumptions based on prior knowledge of the target volume.

With the contamination layer included or taken into account in the inverse mapping in any appropriate manner, it is possible to determine an estimate of the effect of the contamination layer on the observations. Thereby, presence of possible contamination layer on the measurement probe and the interface surfaces thereof may be taken into account, resulting in more reliable determination of the profile of the electrical property of interest.

In addition to the estimation of the electrical property of interest of material(s) in the target volume outside the possible contaminant layer, it is further possible to determine by the method 700 of FIG. 7, on the basis of the adjusted approximation of the electrical property of interest, also an estimate of the properties of the contamination layer itself.

In the above, the method 700 of FIG. 7 is described with regard to one specific instantaneous or stationary situation in the target volume only. Naturally, the method may be applied also for continuous monitoring of the target volume, wherein the situation in the target volume, in particular the electrical property of interest conditions therein, is determined continuously or dynamically, i.e. for different, consequent time instants. Then, the inverse mapping can be constructed to contain models describing the time-dependency of the quantity of interest.

The order of the method operations is not limited to that illustrated in FIG. 7 and explained above. The order of the operations may be any appropriate one. For example, the operation of receiving the measured values of the electrical property of interest may be performed at any stage before it is used as an input for the inverse mapping.

In the above examples and embodiments, a measurement path is specified as being formed between two interface surfaces, enabling using such measurement path in the measurements. It is to be noted, however, that a measurement probe with different measurement paths as defined in the context of any of the above examples and embodiments can also be used to carry out measurements where several interface surfaces are connected or coupled together to form a group of interface surfaces for supplying and/or receiving voltage and/or current signals via such group. Then, a measurement path may be considered as being formed between two groups of interface surfaces instead of two individual interface surfaces. One or both of such groups may comprise a plurality of discrete interface surfaces.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

It will be understood that the benefits and advantages described above may relate to one embodiment or may relate to several embodiments. The embodiments are not limited to those that solve any or all of the stated problems or those that have any or all of the stated benefits and advantages. It will further be understood that reference to 'an' item refers to one or more of those items.

The term "comprising" is used in this specification to mean including the feature(s) or act(s) followed thereafter, without excluding the presence of one or more additional features or acts.

It is to be noted that the embodiments of the claims are not limited to those discussed above, but further embodiments may exist within the scope of the claims.

The invention claimed is:

1. An apparatus for determining, by electrical tomography, vertical profile of an electrical property of interest of material(s) present in a target volume in a container on the basis of measurements of a measurable electrical quantity dependent on said electrical property of interest, the apparatus comprising:

a measurement probe arranged to be positioned at a plurality of different, vertically separate measurement levels in a target volume to carry out the measurements of the measurable electrical quantity at the different measurement levels, the measurement probe comprising;

a plurality of measurement elements each having an interface surface arranged to be, with the measurement probe positioned within the target volume, in measurement connection with the material(s) present in the target volume; each interface surface having a size, a shape, and a rotational position; a measurement path for measurement of the measurable electrical quantity being formed, with the measurement probe in use, between two interface surfaces, the measurement path being dependent on the sizes of, the shapes of, and the rotational positions of the two interface surfaces, and the distance between the two interface surfaces along the surface of the measurement probe; the locations, rotational positions, shapes, and sizes of the interface surfaces of the plurality of measurement elements being selected to provide at least two different measurement paths differing from each other in one or more of said sizes of, shapes of, rotational positions of, and distances between the associated interface surfaces, the apparatus further comprising;

a computing system configured to determine a vertical profile of an electrical property interest of material(s) present in a target volume on the basis of measurements of a measurable electrical quantity dependent on said electrical property of interest, carried out at different measurement levels by the measurement probe; the measurements being carried out, at least for one measurement level, via at least two different measurement paths; wherein determining the profile of the electrical property of interest comprises determining an effect of possible contaminant, accumulated on the interface surface of a measurement element, on the measurements on the basis of the measurements of the measurable electrical quantity via the at least two different measurement paths.

2. The apparatus as defined in claim 1, the distance between two interface surfaces along the surface of the measurement probe being defined by a connecting line, wherein the connecting lines associated to the at least two different measurement paths extend at a non-zero angle relative to each other.

3. The apparatus as defined in claim 1, the measurement probe having a principal axis and being arranged to be positioned at the different measurement levels with the principal axis oriented substantially vertically.

4. The apparatus as defined in claim 3, wherein the interface surfaces of the measurement elements are positioned so as to lie at two or more different planes lying perpendicularly to the principal axis.

5. The apparatus as defined in claim 3, wherein the interface surface of a measurement element has a width in a direction perpendicular to the principal axis, and a length in a direction parallel to the principal axis, the length of the interface surface being substantially larger than the width, for example, at least twice the width.

6. The apparatus as defined in claim 1, wherein the measurement probe comprises an electrically insulating layer covering the interface surfaces of the measurement elements.

7. The apparatus as defined in claim 1, comprising an anchoring arrangement for being anchored in a support structure of a container having the target volume in it, the measurement probe being connected to the anchoring arrangement so as to be vertically movably suspended therefrom.

8. The apparatus as defined in claim 1, wherein the electrical property of interest is electrical admittivity, permittivity, or conductivity.

9. A computing system configured to determine a vertical profile of an electrical property of interest of material(s) present in a target volume on the basis of measurements of a measurable electrical quantity dependent on said electrical property of interest, carried out at different measurement levels by a measurement probe arranged to be positioned at a plurality of different, vertically separate measurement levels in the target volume to carry out the measurements of the measurable electrical quantity at the different measurement levels, the measurement probe comprising:

a plurality of measurement elements each having an interface surface arranged to be, with the measurement probe positioned within the target volume, in measurement connection with the material(s) present in the target volume; each interface surface having a size, a shape, and a rotational position; a measurement path for measurement of the measurable electrical quantity being formed, with the measurement probe in use, between two interface surfaces, the measurement path being dependent on the sizes of, the shapes of, and the rotational positions of the two interface surfaces, and the distance between the two interface surfaces along the surface of the measurement probe; the locations, rotational positions, shapes, and sizes of the interface surfaces of the plurality of measurement elements being selected to provide at least two different measurement paths differing from each other in one or more of said sizes of, shapes of, rotational positions of, and distances between the associated interface surfaces;

the measurements being carried out, at least for one measurement level, via at least two different measurement paths; wherein determining the profile of the electrical property of interest comprises determining an effect of possible contaminant, accumulated on the interface surface of a measurement element, on the measurements on the basis of the measurements of the measurable electrical quantity via the at least two different measurement paths.

10. An electrical tomography method for determining a vertical profile of an electrical property of interest of material(s) present in a target volume in a container on the basis of measurements of a measurable electrical quantity dependent on said electrical property of interest, carried out at a plurality of different measurement levels by an apparatus as defined in claim 1; the measurements being carried out, at least for one measurement level, via at least two different measurement paths; wherein determining the profile of the electrical property of interest comprises determining an effect of possible contaminant, accumulated on the interface surface of a measurement elements on the measurements, on the basis of the measurements of the measurable electrical quantity via the at least two different measurement paths.

11. The method as defined in claim 10, wherein the electrical property of interest is electrical admittivity, permittivity, or conductivity.

12. The method as defined in claim 10, wherein the target volume comprises oil, and the electrical property of interest is dependent on water content of the oil.

13. A computer program product comprising program code instructions which, when executed by a processor, cause the processor to perform the method according to claim 10.

14. The computer program product as defined in claim 13, stored on a computer-readable medium.

* * * * *